United States Patent

Barrish et al.

[11] Patent Number: 5,492,910
[45] Date of Patent: Feb. 20, 1996

[54] RETROCARBAMATE PROTEASE INHIBITORS

[75] Inventors: Joel C. Barrish, Holland; Steven H. Spergel, Bensalem, both of Pa.

[73] Assignee: Bristol-Myers Squibb Co., Princeton, N.J.

[21] Appl. No.: 341,245

[22] Filed: Nov. 17, 1994

[51] Int. Cl.⁶ .................. C07D 265/30; C07C 271/00; A61K 38/05; A61K 38/06
[52] U.S. Cl. .............. 514/237.5; 544/168; 560/115; 514/478; 514/18; 514/19
[58] Field of Search ............... 560/115; 544/168; 514/478, 237.5

[56] References Cited

FOREIGN PATENT DOCUMENTS 580402  1/1994  European Pat. Off. .

*Primary Examiner*—Joseph K. McKane
*Assistant Examiner*—Laura L. Stockton
*Attorney, Agent, or Firm*—Stephen B. Davis

[57] ABSTRACT

The invention discloses compounds of the formula

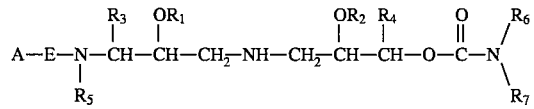

are disclosed as HIV protease inhibitors.

10 Claims, No Drawings

RETROCARBAMATE PROTEASE INHIBITORS

BACKGROUND OF THE INVENTION

Gordon et al. in European Patent Application 580,402 disclose protease inhibitors of the formula

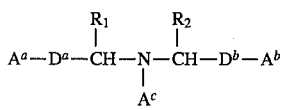

SUMMARY OF THE INVENTION

This invention is directed to the protease inhibiting retrocarbamate compounds of formula I and salts thereof, to pharmaceutical compositions containing such compounds, and to the method of using such compounds.

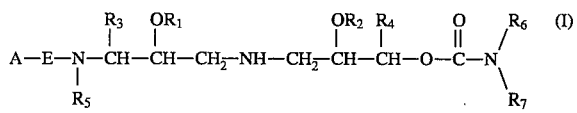

wherein:

$R_1$ and $R_2$ are independently selected from hydrogen, alkyl, substituted alkyl, alkylene-aryl, and alkylene-substituted aryl.

$R_3$ and $R_4$ are independently selected from hydrogen, alkyl, substituted alkyl, cycloalkyl, aryl, substituted aryl, alkylene-aryl, alkylene-substituted aryl, alkylene-cycloalkyl, and alkylene-heterocyclo.

$R_5$ is hydrogen, alkyl, substituted alkyl, alkylene-aryl, or alkylene-substituted aryl.

$R_6$ and $R_7$ are independently selected from hydrogen, alkyl, substituted alkyl, alkylene-aryl, or alkylene-substituted aryl or $R_6$ and $R_7$ taken together with the N-atom to which they are attached complete a heterocyclic ring of 5 to 7 atoms.

A is hydrogen, alkyl,

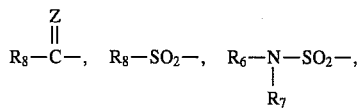

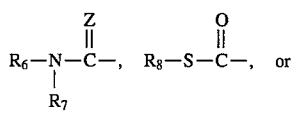

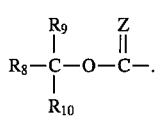

$R_8$, $R_9$ and $R_{10}$ are independently selected from hydrogen, alkyl, substituted alkyl, cycloalkyl, aryl, substituted aryl, alkylene-cycloalkyl, alkylene-aryl, and alkylene-substituted aryl or $R_8$ and $R_9$ join together to complete a carbocyclic ring of 3 to 7 carbon atoms.

Z is oxygen or sulfur.

E is a single bond or a peptidyl chain containing 1 to 4 amino acids the N-terminus of which is bonded to A, i.e. A—E is

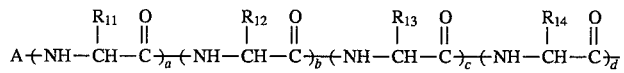

wherein a, b, c, and d are each zero or one and $R_{11}$, $R_{12}$, $R_{13}$ and $R_{14}$ are independently selected from hydrogen, alkyl, substituted alkyl, alkylene-aryl, alkylene-substituted aryl, and alkylene-heterocyclo.

DETAILED DESCRIPTION OF THE INVENTION

This invention in its broadest aspects relates to the compounds of formula I above, to compositions and the method of using such compounds to inhibit protease and thus produce a beneficial pharmaceutical effect.

The term alkyl used in defining various symbols refers to straight and branched chain radicals of 1 to 10 carbons. Preferred alkyl groups are those of 1 to 6 carbons.

The term substituted alkyl used in defining various symbols refers to such alkyl groups as defined above wherein one, two or three hydrogens, preferably one, have been replaced by a halo, hydroxy, amino, —NH(alkyl or 1 to 4 carbons), —N(alkyl of 1 to 4 carbons)$_2$, alkoxy of 1 to 4 carbons, alkylthio of 1 to 4 carbons, carboxy, cyano, —O-aryl, —S-aryl, —O-substituted aryl, —S-substituted aryl, —O-alkylene-aryl, —O-alkylene-substituted aryl, —S-alkylene-aryl, —S-alkylene-substituted aryl, —O-alkylene-heterocyclo,

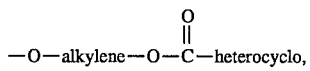

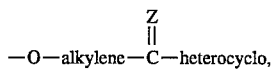

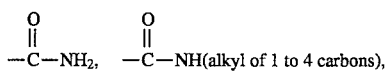

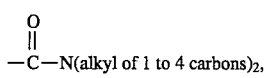

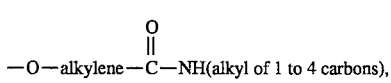

-continued

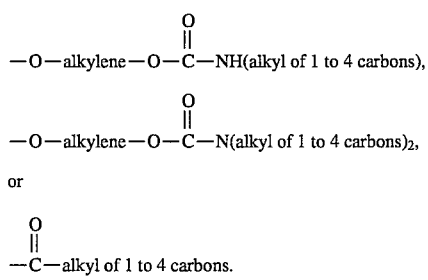

The term aryl used in defining various symbols refers to phenyl, which is preferred, 1-naphthyl, 2-naphthyl, and biphenyl.

The term substituted aryl used in defining various symbols refers to such aryl groups as defined above having one, two or three substituents, preferably one, selected from halo, hydroxy, amino —NH(alkyl of 1 to 4 carbons), —N(alkyl of 1 to 4 carbons)$_2$, nitro, alkyl of 1 to 4 carbons, alkoxy of 1 to 4 carbons, alkylthio of 1 to 4 carbons, —O-phenyl, —S-phenyl, —CH$_2$-phenyl, —O-alkylenephenyl, —S-alkylene-phenyl, —O-alkylene-heterocyclo,

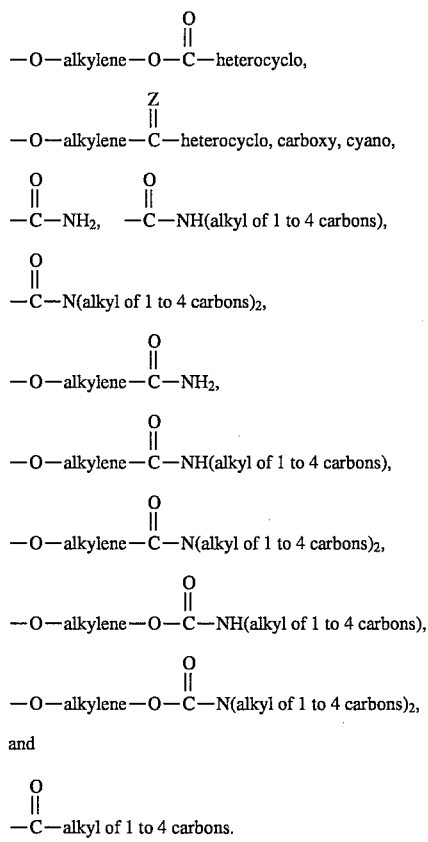

and $$-\overset{O}{\underset{\|}{C}}-\text{alkyl of 1 to 4 carbons.}$$

The term heterocyclo used in defining various symbols refers to fully saturated, partially saturated, or unsaturated rings of 5, 6 or 7 atoms containing one or two oxygen or sulfur atoms and/or one to four nitrogen atoms provided that the total number of hetero atoms in the ring is 4 or less. Preferred heterocyclo groups include 2-,3-, or 4-pyridyl, 2-pyrazinyl, 4-pyridazinyl, 4-imidazolyl, 4-thiazolyl, 2- and 3-thienyl, 2- and 3-furyl, 3-oxazolidinyl, and N-morpholinyl. The term heterocyclo also includes bicyclic rings wherein the five or six membered ring containing O, S, and N atoms as defined above is fused to a benzene or pyridyl ring. A preferred bicyclic ring is indolyl. The mono or bicyclic heterocyclic ring can also be additionally substituted at an available carbon atom by an alkyl of 1 to 4 carbons, halo substituted alkyl of 1 to 4 carbons, keto, hydroxy, benzyl or cyclohexylmethyl, such as, 2-oxo-3-oxazolidinyl which is a preferred heterocyclo group. Also, if the mono or bicyclic heterocyclic ring has an available N atom such N atom can be substituted with an N-protecting group such as phenylmethoxymethyl, tolyl, 2,4-dinitrophenyl, alkyl of 1 to 4 carbons, benzyl or benzhydryl.

The term alkylene used in defining various symbols refers to a straight chain bridge of 1 to 7 carbons connected by single bonds, i.e. —(CH$_2$)$_n$— wherein n is an integer from 1 to 7, and such straight chain bridge of 1 to 7 carbons wherein one, two or three hydrogens have been replaced by an alkyl of 1 to 4 carbons, i.e.

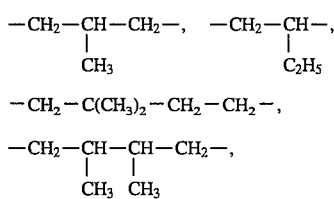

etc., a hydroxy or hydroxy substituted alkyl of 1 to 4 carbons, i.e.

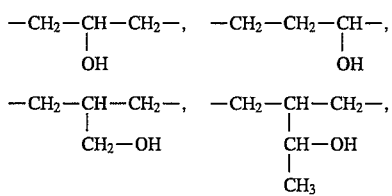

etc., an amino or amino substituted alkyl of 1 to 4 carbons, i.e.

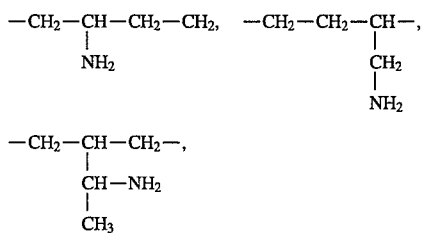

etc.

The term halo used in defining various symbols refers to chloro, bromo, fluoro and iodo.

The term salts denotes acidic and/or basic salts formed with inorganic and/or organic acids and bases. Zwitterions (internal or inner salts) are included within the term salts, as are quaternary ammonium salts such as alkylammonium salts. The nontoxic, pharmaceutically acceptable salts are preferred, although other salts may be useful, for example, in isolation or purification steps which may be employed during preparation.

Exemplary acid addition salts include acetate, adipate, aliginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, thiocyanate, tosylate, and undecanoate.

If the product of formula I contains an acidic group then basic salts can be prepared. Exemplary basic salts include ammonium salts, alkali metal salts such as sodium, lithium, and potassium salts, alkaline earth metal salts such as calcium and magnesium salts, salts with organic bases such as dicyclohexylamine, N-methyl-D-glucamine, and salts with amino acids such as arginine, lysine and so forth. The basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of formula I are also part of this invention. The term prodrug denotes a compound which, upon administration to a subject, undergoes chemical conversion by metabolic or chemical processes to yield a compound of the formula I, or a salt and/or solvate thereof. See H. Bundgaard, "Drugs of the Future", 16 (5), 443–458 (1991); and H. Bundgaard (Ed), "Design of Prodrugs" 1985 Elsevier (Amsterdam), both incorporated herein by reference.

Solvates of the compounds of formula I are preferably hydrates. Tautomers of the inventive compounds are also contemplated, such as hemiketals of hydroxyketones, the enol form of ketones, and the like.

All stereoisomers of the present compounds are contemplated within the scope of this invention. Individual stereoisomers of the compounds of the invention may, for example, be substantially free of other isomers, or may be admixed, for example, as racemates. The chiral centers of the present invention can have the S or R configuration as defined by the IUPAC 1974 Recommendations.

A description of exemplary methods for obtaining the compounds of the present invention follows. The reaction conditions of these methods, such as temperature, amount of reagent, pressure, reaction time, atmosphere and solvent employed may readily be ascertained by one of ordinary skill in the art.

The compounds of formula I wherein E is a single bond, A is other than hydrogen, and $R_1$ and $R_2$ are both hydrogen can be prepared by reacting an amino alcohol of the formula

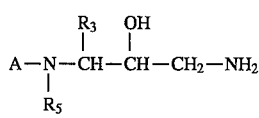

with an epoxide of the formula

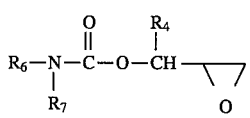

with heat in an organic solvent such as dimethylformamide.

The compounds of formula I wherein E is a single bond, A is other than hydrogen, and $R_1$ and $R_2$ are both hydrogen can also be prepared by treating the epoxide of formula III with an azide anion such as sodium azide to open the epoxide ring (Ingham et al. J. Org. Chem., 21, 373 (1956); Rosenberg et al., J. Med. Chem. 32, 1371 (1989); Saito et al., Tetrahedron Letters, 30, 4153 (1989)] and give the azido compound of formula

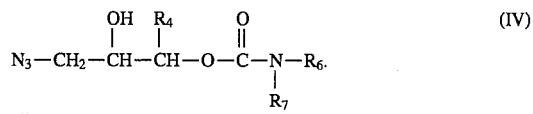

The azido compound of formula IV can then be reduced such as by hydrogenation over palladium on carbon catalyst or by treatment with triphenylphosphine [Vaultier et al., Tetrahedron Letters, 24 763 (1983)] to give the amino alcohol of the formula

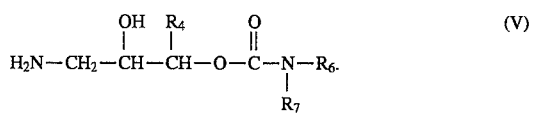

The amino alcohol of formula V can then be coupled to the epoxide of the formula

as described above to give the desired products of formula I.

When A in the above reactions is a nitrogen protecting group such as benzyloxycarbonyl, t-butoxycarbonyl, benzyl, etc., the product can be treated according to known methods to remove the protecting group and yield the corresponding product of formula I wherein A is hydrogen and E is a single bond. The resulting amine product can be coupled with the amino acid or peptidyl compound of the formula

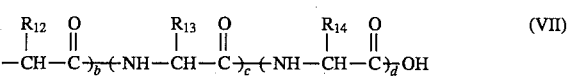

using standard methodology. The above reaction can be performed in the presence of a coupling reagent such as dicyclohexylcarbodiimide, 3-ethyl-3'-(dimethylamino)propylcarbodiimide, bis-(2-oxo-3-oxazolidinyl)phosphinic chloride, benzotriazol-1-yloxytris(dimethylamino)phosphonium hexafluorophosphate, diphenylphosphoryl azide, etc.

The products of formula I wherein E is a single bond, A is other than hydrogen, and $R_1$ and $R_2$ are both hydrogen can also be prepared by reacting the amino alcohol of formula V with the aldehyde of the formula

under reductive amination conditions. For example, hydrogenation over palladium on carbon catalyst or reaction with sodium cyanoborohydride.

The products of formula I wherein E is a single bond, A is other than hydrogen, $R_7$ is hydrogen, and $R_1$ and $R_2$ are both hydrogen can also be prepared by reacting the amino alcohol of formula II with the aldehyde of the formula

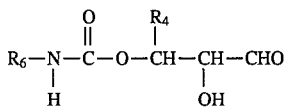 (IX)

under reductive amination conditions.

The aldehyde of formula IX can be prepared by reacting an aldehyde of the formula

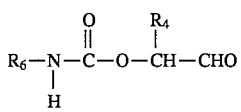 (X)

with a vinylorganometallic reagent such as vinylmagnesium bromide, vinylcerium or vinyllithium followed by oxidative cleavage of the olefin with ozone followed by treatment with dimethylsulfide or potassium permanganate or osmium tetraoxide/sodium metaperiodate.

The epoxide intermediate of formula III wherein $R_7$ is hydrogen can be prepared by reacting the aldehyde of the formula (XI)

$R_4$—CHO with a vinylorganometallic reagent such as vinylmagnesium bromide, vinylcerium or vinyllithium to give the alcohol of the formula

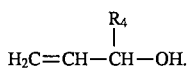 (XII)

The alcohol of formula XII can be epoxidized using a reagent such as m-chloroperbenzoic acid to give the epoxyalcohol of the formula

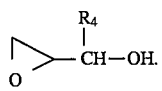 (XIII)

Reaction of the epoxyalcohol of formula XIII with an isocyanate of the formula (XIV)

$R_6$—N=C=O or carbamoyl chloride of the formula

 (XV)

in the presence of an alkylamine base such as triethylamine gives the epoxide intermediate of formula III.

Alternatively, the epoxide of formula III can be obtained by reversing the order of the steps described above. Thus, the alcohol of formula XII could first be treated with the isocyanate of formula XIV or the carbamoyl chloride of formula XV to give the intermediate of the formula

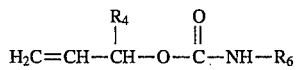 (XVI)

Epoxidation of the intermediate of formula XVI using a reagent such as in chloroperbenzoic acid gives the desired epoxide of formula III.

The intermediate of formula III can also be prepared in chiral form as follows. The alcohol of formula XII can be treated with (+)-diisopropyl tartrate, titanium isopropoxide and t-butyl hydroperoxide to give the chiral epoxyalcohol of the formula

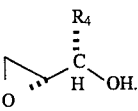 (XVII)

This methodology is described by Sharpless [J. Am. Chem. Soc., 103, 6237 (1981)]. The chiral epoxyalcohol of formula XVII can then be reacted with the isocyanate of formula XIV or the carbamoyl chloride of formula XV to give the intermediate of formula III in chiral form shown below as formula

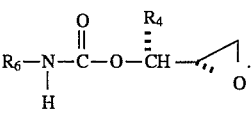 (IIIa)

In an alternate procedure, the intermediate of formula III can be prepared as follows. A hydroxyester of the formula

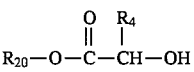 (XVIII)

wherein $R_{20}$ is methyl, ethyl, or benzyl, prepared by methods known in the art, can be treated with the isocyanate of formula XIV or the carbamoyl chloride of formula XV in the presence of an alkyl amine base such as triethylamine to give the carbamate of the formula

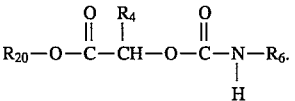 (XIX)

Removal of the $R_{20}$ group such as by treatment with base, for example, lithium hydroxide, sodium hydroxide, or potassium hydroxide gives the acid of the formula

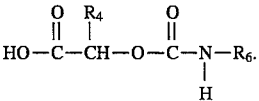 (XX)

The acid of formula XX can then be converted to an activated form such as an acid chloride by reaction with thionyl chloride or oxalyl chloride or to a mixed anhydride by reaction with a chloroformate of the formula

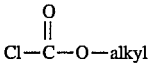

and then treated with diazomethane to give the diazoketone of the formula

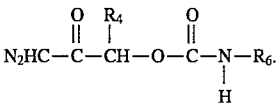 (XXI)

Treatment of the diazoketone of formula XXI with hydrochloric acid, hydrobromic acid, or hydriodic acid gives the α-ketone of the formula

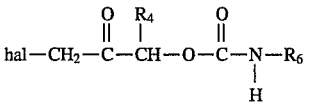 (XXII)

wherein hal is Cl, Br, or I. Treatment of the α-haloketone of formula XXII with a reducing agent gives the halohydrin of the formula

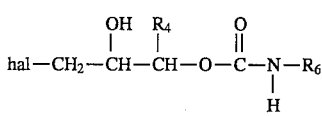

(XXIII)

which can then be converted to the epoxide intermediate of formula III by known methods, e.g. Handa et al. European Patent Application 346,847; Rich et al., J. Med. Chem., 34, 1222 (1991). According to these known methods, the α-haloketone of formula XXII can be reduced with a hydride reducing agent such as lithium aluminum hydride, sodium borohydride, potassium borohydride, diisobutylaluminum hydride, lithium tri-sec-butylborohydride, or potassium tri-sec-butylborohydride to give the halohydrin of formula XXIII which can then be converted to the epoxide of formula III by treatment with base such as sodium or potassium hydride, sodium of potassium hydroxide, or an alkyl amine base such as triethylamine.

In another alternate procedure, the alcohol of formula XII can be treated with the isocyanate of formula XIV or the carbamoyl chloride of formula XV as described above and the resulting olefin can be oxidatively cleaved using reagents such as ozone followed by dimethylsulfide, or potassium permanganate, or osmium tetraoxide/sodium metaperiodate to give the aldehyde of formula X. The aldehyde of formula X can be converted directly to the epoxide of formula III by reaction with sulfonium or arsonium ylide as note Corey et al., J. Amer. Chem. Soc., 87, 1353 (1965) and Still et al., J. Amer. Chem. Soc., 103, 1283 (1981).

In another alternate procedure, the alcohol of formula XII can be treated with the isocyanate of formula XIV or the carbamoyl chloride of formula XV as described above and the resulting olefin can be treated with a compound of the formula (XXIV)

Ho—hal    (XXIV)

wherein hal is chloro, bromo, or iodo to give the halohydrin of formula XXIII which can then be converted to the epoxide of formula III as described above. The reagent of formula XXIV can be formed in situ, for example, by contacting N-chlorosuccinimide, N-bromosuccinimide, N-iodosuccinimide, bromine, iodine, or chlorine with water.

The intermediate of formula III wherein $R_6$ and $R_7$ are other than hydrogen can be prepared as follows. The epoxyalcohol of formula XIII or the chiral epoxyalcohol of formula XVII can be directly coupled with the carbamoyl chloride of the formula

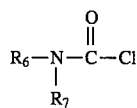

(XXV)

to give the desired intermediate of formula III wherein $R_6$ and $R_7$ are other than hydrogen.

Alternatively, the alcohol of formula XII can be coupled with the carbamoyl chloride of formula XXV to give the compound of the formula

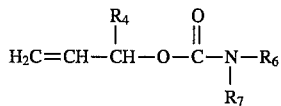

(XXVI)

which can then be converted to the epoxide intermediate of formula III wherein $R_6$ and $R_7$ are other than hydrogen using procedures described above. As a further alternative, the hydroxyester of formula XVIII can be coupled with the carbamoyl chloride of formula XXV to give the compound of the formula

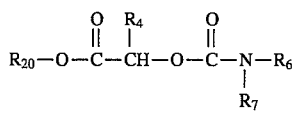

(XXVII)

which can then be converted to the epoxide intermediate of III wherein $R_6$ and $R_7$ are other than hydrogen using procedures described above.

Alternatively, the intermediate of formula XXVI can also be prepared by treating the intermediate of formula XVI with base such as sodium or potassium hydroxide or potassium or cesium carbonate followed by reaction with a compound of the formula (XXVIII)

$R_7$—X wherein X is a leaving group, for example, chloro, bromo, p-toluenesulfonyl, methanesulfonyl, trifluoromethanesulfonyl, etc.

The products of formula I wherein $R_2$ is other than hydrogen can be prepared by treating the azido compound of formula IV with a base, such as sodium or potassium hydride or sodium or cesium carbonate, followed by reaction with a compound of the formula (XXIX)

$R_2$—X wherein X is as defined above and $R_2$ is other than hydrogen to give the compound of the formula

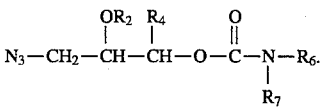

(XXX)

The azido of formula XXX can then be reduced such as by hydrogenation over palladium on carbon catalyst or by treatment with triphenylphosphine to give the amino compound of the formula

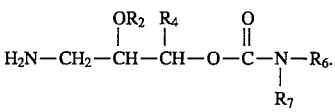

(XXXI)

The amino compound of formula XXXI can then be coupled to the epoxide of formula VI as described above to give the desired products of formula I.

The products of formula I wherein $R_1$ is other than hydrogen can be prepared by treating the epoxide of formula VI with an azide anion such as sodium azide to open the epoxide ring and give the azido compound of the formula

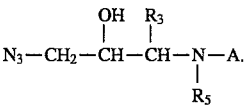

(XXXII)

Treating the azido compound of formula XXXII with base, such as sodium or potassium hydride or sodium or potassium hydroxide or sodium or cesium carbonate, followed by reaction with a compound of the formula (XXXIII)

$R_1$—X wherein X is as defined above and $R_1$ is other than hydrogen gives the compound of formula

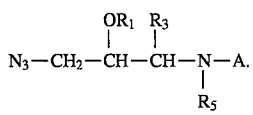

(XXXIV)

The azido compound of formula XXXIV can then be reduced such as by hydrogenation over palladium on carbon catalyst or by treatment with triphenylphosphine to give the amino compound of the formula

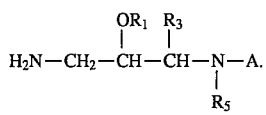

(XXXV)

The amino compound of formula XXXV can then be coupled to the epoxide of formula III as described above to give the desired products of formula I.

The compounds of formula I wherein E is a single bond and A is hydrogen can be prepared by treating a compound of formula I wherein E is a single bond and A is t-butoxycarbonyl or benzyloxycarbonyl. For example, treatment with acid such as trifluoroacetic acid removes the t-butoxycarbonyl group and hydrogenation removes the benzyloxycarbonyl group to yield the desired products of formula I wherein E is a single bond and A is hydrogen.

The compounds of formula I wherein A is hydrogen and E is a single bond can be reacted with the peptidyl moiety

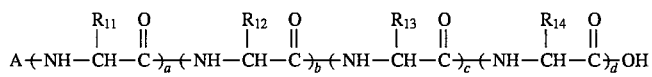

(XXXVI)

to give other products of formula I. This reaction is preferably performed in the presence of a coupling reagent such as dicyclohexylcarbodiimide, benzotriazol-1-yloxy-tris(dimethylamino)phosphonium hexafluorophosphate, diphenylphosphoryl azide, etc. Techniques for peptide couplings are well known in the art. For example, see Bodansky, "Principles of Peptide Synthesis", Springer-Verlag (1984).

The amino alcohol starting materials of formula II, the epoxide reagents of formula VI, and the aldehydes of formula VIII are known compounds or are compounds which can be readily prepared by known methods, as note, for example, European Patent Application 580,402.

Preferred compounds of this invention are those of formula I wherein:

E is a single bond.

$R_1$ and $R_2$ are both hydrogen.

A is

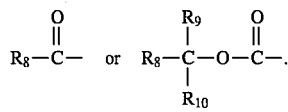

$R_3$ and $R_4$ are independently selected from alkylene-aryl and alkylene-substituted aryl.

$R_5$ is hydrogen.

$R_6$ is alkyl or substituted alkyl.

$R_7$ is hydrogen.

$R_8$, $R_9$, and $R_{10}$ are independently selected from alkyl and substituted alkyl.

The compounds of the present invention inhibit retroviral proteases, thereby inhibiting viral replication, and are thus especially useful in the treatment and/or prevention of retroviral infections caused by such pathogenic organisms.

Proteases are enzymes which cleave proteins at specific peptide bonds and, in living systems, mediate or control a broad spectrum of biological functions, such as cleaving precursors to form active proteins in post translational processing of polypeptides. For example, retroviral proteases cleave large precursor polypeptides, produced in infected cells, into smaller protein components, or subunits, which are subsequently assembled to form functional virus structures. As proteases encoded by the viral genome play a critical role in the replication of a virus, these enzymes represent targets for therapeutic agents.

Retroviruses are viruses which contain two copies of their RNA genome, each of which is copied into a double strand of DNA using a retroviral enzyme reverse transcriptase (RT). A second retroviral enzyme, ribonuclease H, is part of the RT protein and facilitates the synthesis of the DNA:DNA duplex. A third retroviral enzyme called integrase splices the double standed DNA copy of the virus into the chromosome of the host cell. A fourth retroviral enzyme cell protease is critical to the process of viral replication by cleaving polypeptide precursors into required enzymes and structural proteins.

Exemplary protease-encoding retroviruses, the replication of which may be inhibited by the compounds of the present invention include the human T-cell lymphotrophic viruses, HTLV-I and HTLV-II, the human immunodeficiency viruses, for example HIV-1, HIV-2 or mutants thereof (AIDS pathogens), feline leukemia virus and simian immunodeficiency virus. Protease inhibition may be assayed by methods such as those described below in the Examples section of the present specification. The compounds of the present invention may, of course, be used to simultaneously inhibit the replication of two or more retroviruses, as well as to inhibit the replication of a single retrovirus.

The compounds of the present invention are particularly useful in the inhibition of human immunodeficiency virus (HIV) protease, and thus in the prevention and/or treatment of infection by HIV viruses (HIV-1, HIV-2 and mutants thereof), including the treatment of consequent pathological conditions such as AIDS.

HIV protease is a retroviral protease which processes the gag polyprotein precursor into core proteins and the pol polyprotein precursor into reverse transcriptase, integrase, and the protease itself. HIV protease is essential for the correct processing of these polyproteins and the production of infectious viral particles, as evidenced by the fact that mutations of the protease gene result in non-infectious viral particles with an immature morphology. Inhibition of HIV protease is thus a highly attractive target for anti-HIV therapy.

Use of the compounds of the present invention in inhibiting HIV protease includes, but is not limited to, treating a wide range of states of HIV infection such as treating or preventing AIDS or ARC (AIDS related complex), treating both symptomatic and asymptomatic HIV-infected patients, and treating actual or potential exposure to HIV. For example, the compounds of this invention are useful in treating infection by HIV after suspected past exposure to HIV by, e.g., blood transfusion, accidental needle stick, or exposure to patient blood during surgery.

As indicated above, the compounds of the present invention may also be useful in the treatment and/or prevention of infections caused by other retroviruses. Exemplary retroviruses that are pathogenic in man and in addition to the human immunodeficiency viruses are HTLV-1 and HTLV-2.

Exemplary viruses pathogenic in other species are feline leukemia virus and simian immunodeficiency virus.

The present invention also provides pharmaceutical compositions comprising at least one of the inventive compounds capable of inhibiting retroviral protease in an amount effective therefor, and a pharmaceutically acceptable vehicle or diluent. The compositions of the present invention may be formulated, for example, by employing conventional solid or liquid vehicles or diluents, as well as pharmaceutical additives of a type appropriate to the mode of desired administration. The compounds may, for example, be administered orally, such as in the form of tables, capsules, granules or powders; parenterally, such as by subcutaneous, intravenous, intramuscular or intrasternal injection or infusion techniques (e.g. as sterile injectable aqueous or nonaqueous solutions or suspension); nasally such as by inhalation spray; or rectally such as in the form of suppositories; in dosage unit formulations containing non-toxic, pharmaceutically acceptable vehicles or diluents. The present compounds may, for example, be administered liposomally.

When administered orally, the compositions may be prepared according to techniques well known in the art of pharmaceutical formulation. As a suspension they may, for example, contain microcrystalline cellulose for imparting bulk, alginic acid or sodium alginate as a suspending agent, methylcellulose as a viscosity enhancer, and sweeteners or flavoring agents known in the art. As immediate release tables, the present compositions may contain microcrystalline cellulose, dicalcium phosphate, starch, magnesium stearate and/or lactose and/or other excipients, binders, extenders, disintegrants, diluents and lubricants known in the art.

When administered by nasal aerosol or inhalation, the compositions may be prepared according to techniques well known in the art of pharmaceutical formulation and may be prepared as solutions in saline, employing benzyl alcohol or other suitable preservatives, absorption promoters to enhance bioavailability and/or other solubilizing or dispersing agents known in the art.

When administered as injectable solutions or suspension, the present compositions may be formulated according to techniques well known in the pharmaceutical art, using suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

When rectally administered in the form of suppositories, these compositions may be prepared by techniques well known in the pharmaceutical art by mixing the drug with a suitable non-irritating excipient, such as cocoa butter, synthetic glyceride esters or polyethylene glycols, which are solid at ordinary temperatures, but liquify and/or dissolve in the rectal cavity to release the drug.

The pharmaceutical compositions of the present invention may contain an amount of the inventive compounds effective for the inhibition of retroviral replication and preferably an amount effective for the treatment and/or prevention of infection by HIV. The effective amount of a compound of the present invention may be determined by one of ordinary skill in the art, and includes amounts such as those from about 1 to 150 mg/kg of body weight of active compound per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination and severity of the particular condition.

Viral hosts which are preferred subject for treatment and/or prevention of retroviral infections include animals, most preferably mammalian species such as humans, and domestic animals such as dogs, cats and the like. A dose for adult humans is preferably between 10 and about 50 mg/kg of body weight per day, which may be administered in a single or in the form of individual divided doses, such as from 1–4 times per day.

The compounds of the present invention may be employed alone or in combination with other suitable therapeutic agents useful in the treatment of retroviral infections such as AIDS, such as other antiviral agents, immunomodulators, antibiotics or vaccines.

Other therapeutic agents may include, but are not restricted to the following: antivirals exemplified by AL-721, interferon beta, polymannoacetate, ganciclovir, DDC (dideoxycytidine), d4T, DDI (dideoxyinosine), Foscarnet (trisodium phosphonoformate), HPA-23, eflornithine, Peptide T (octapeptide sequence), Reticulose (nucleophosphoprotein), AZT, ansamycin LM 427, trimetrexate, UA-001, ribavirin, α-interferon, acyclovir, 3TC, PMEA, nevirapine, pyridinones (e.g. L-697,661), BHAPs (e.g. U-90152), alpha-APA derivatives (e.g. R 18893), TIBO derivatives (e.g. $R_{82913}$, Ro 31-8959, SC 52151, A-77003, A-80987, A-84538, and L-737,524); immunomodulators exemplified by bropirimine, Ampligen (mismatched RNA), Anti-human alpha interferon antibody, Colony Stimulating Factor (GM-CSF), CL246,738, IMREG-1, IMREG-2, diethyl dithio carbamate, interleukin-2, inosine pranobex, methionine enkephalin, MTP-PE (muramyl-tripeptide), Thymypentin (TP-5) (thymic compound), recombinant erythropoietin, naltrexone, TNF (tumor necrosis factor); and antibiotics exemplified by Pentam 300 (pentamidine isethionate).

In particular, the HIV protease inhibitors of the present invention may be used in combination with other antiretroviral therapies for the treatment of AIDS. Such combined therapies may include, but are not limited to, a compound of the present invention in combination with: other (e.g., those other than inhibitors of the present invention) HIV protease inhibitors (e.g. Ro 31-8959, SC 52151, A-77003, A- 80987, A-84538 and L-737,524); nucleoside and non-nucleoside reverse transcriptase inhibitors preferably nucleoside reverse transcriptase inhibitors such as AZT, DD1, d4T, DDC, 3TC, or PMEA, and non-nucleoside reverse transcriptase inhibitors such as nevirapine, pyridinones (e.g. L-697,661), BHAPs (e.g. U-90152), alpha-APA derivatives (e.g., R 18893) and TIBO derivatives (e.g. R82913); inhibitors of tat such as RO24-7429; drugs which inhibit binding of the virus to $CD_4$ receptors; inhibitors of RNase, integrase, or rev; and immunomodulators such as IFN-α (α-interferon).

The above compounds to be employed in combination with the compounds of the present invention will be used, for example, in amounts as indicated in the Physicians' Desk Reference (PDR) or as otherwise determined by one of ordinary skill in the art. The aforementioned combined therapies may, for example, be conducted simultaneously or sequentially.

The instant invention also provides methods for the inhibition of retroviral proteases by contacting said protease with a compound of the present invention capable of said inhibition, and particularly for the treatment and/or prevention of retroviral infections. Treatment and/or prevention of infection by the human immunodeficiency viruses is preferred. The methods of the present invention preferably comprise the step of administering to a subject in need thereof one or more of the present compounds capable of treatment and/or prevention of retroviral infection in an amount effective therefor. Other therapeutic agents such as those described above may be employed with the inventive compounds in the present methods.

The compounds of the present invention are also useful in the preparation of other compounds of the formula I. Thus, for example, one compound of the present invention may be employed in the preparation of another compound of the present invention, where the latter compound has greater potency against the same or different retrovirus than the former.

The following Examples will serve to illustrate the preparation of compounds of the present invention, and are not intended to limit the scope or spirit of the instant claims.

EXAMPLE 1

[1S-[1R*,2S*(2S*,3R*)]]-[3-[[3-[[[
(1,1-Dimethylethyl)amino]carbonyl]oxy]-2
-hydroxy-4-phenylbutyl]amino]-2-hydroxy-1
-(phenylmethyl)-propyl]carbamic acid, 1,1-dimethyl
ester a) α-Ethenylbenzenethanol A solution of phenylacetaldehyde(600 mg, 5 mmol) in 12 ml of tetrahydrofuran was added dropwise over about 10 minutes to a solution of vinyl magnesium bromide (10 ml; 1M in tetrahydrofuran; 10 mmol) in 12 ml of tetrahydrofuran at 0° C. The internal temperature was maintained below 5° C. during the addition. After stirring for 1 hour at 0° C., the reaction was quenched by adding about 25 ml of saturated ammonium chloride solution. The resulting mixture was extracted with 100 ml of ethyl ether. The organic layer was washed with saturated ammonium chloride solution(50 ml) and brine(50 ml). Drying over magnesium sulfate and concentrating afforded 750 mg of the title product as a light orange liquid.

b) [R-(R*,S*)]-α-Oxiranylbenzenethanol (+)-Diisopropyl tartrate(0.84 ml; 3.96 mmol), titanium isopropoxide(0.74 ml, 2.64 mmol) and t-butyl hydroperoxide(0.28 ml; 5.5M in isooctane; 1.58 mmol) were added sequentially to a solution of the product from part (a) (330 mg, 2.20 mmol) in 25 ml of methylene chloride at –20° C. The resulting solution was stirred at –20° C. for 15 minutes and was allowed to stand at –20° C. for 8 days. This mixture was poured into a solution of 0.74 ml of water in 50 ml of acetone at –20° C. This mixture was allowed to warm to room temperature after which time it became turbid. Celite® was added and the suspension was filtered through a 0.45 micron nylon-66 filter. The filter cake was washed with acetone and the filtrate was concentrated. The residue was dissolved in 12 ml of ether and the resulting solution was cooled to 0° C. with stirring. 1N Sodium hydroxide(12 ml) was added and the biphasic mixture was stirred at 0° C. for 30 minutes. The layers were separated and the organic layer was washed with brine (25 ml), dried over magnesium sulfate and concentrated. The residue was chromatographed on a 2.5×20 cm silica gel column using hexane:ethyl acetate, 4:1 as the mobile phase. The pure fractions were concentrated to afford 113 mg of title product as a colorless liquid.

Anal. calc'd for $C_{10}H_{12}O_2 \cdot 0.21\ H_2O$: C, 71.53; H, 7.45

Found: C, 71.53; H, 7.38.

c) (1,1-Dimethylethyl) carbamic acid, [S-(R*,S*)]-1-oxiranyl-2-phenylethyl ester A mixture of the product from part (b) (90 mg, 0.55 mmol), t-butylisocyanate(0.2 ml, 1.70 mmol) and triethylamine(0.28 ml, 2 mmol) in 1.5 ml of methylene chloride was stirred at room temperature for 6 hours and then heated to 45° C. in a stoppered flask for 24 hours. The volatiles were removed in vacuo and the residue was chromatographed on 2.5×10 cm silica gel column, using hexane:ethyl acetate 4:1 as the mobile phase. The fractions containing the least polar product were concentrated to afford 102 mg of title product as a colorless semisolid.

d) [S-(R*,R*)]-[3-Chloro-2-hydroxy-1-(phenylmethyl) propyl]carbamic acid, 1,1-dimethylethyl ester To the mixture of 40% aqueous potassium hydroxide (75 ml) and ethyl ether (255 ml) cooled at 0° C. was added 1-methyl-3-nitrosoguanidine (23.85 g, 162.2 mmol) portionwise. The mixture was swirled several times during each addition. After 10 minutes, the resulting yellow ethyl ether layer was decanted over potassium hydroxide pellets at 0° C. and dried for 2.0 hours at 0° C. to give a diazomethane-ethyl ether solution.

To a solution of N-[(1,1-dimethylethoxy)carbonyl]-L-phenylalanine (14.34 g, 54.05 mmol) in dry tetrahydrofuran (80 ml) cooled at –20° C. to –25° C. (dry ice-carbon tetrachloride bath) was added isobutyl chloroformate (7.01 ml, 54.05 mmol) over 5 minutes, followed by 4-methylmorpholine (5.94 ml, 54.05 mmol) and the mixture was stirred for 20 minutes. The white precipitate was removed by filtration under an argon atmosphere and washed with about 70 ml of dry tetrahydrofuran. The combined tetrahydrofuran solution of mixed anhydride was cooled to –5° C. and poured into the above prepared diazomethane in ethyl ether solution at 0° C. The resulting yellow solution was kept at 0° C. for 2.0 hours, then room temperature overnight. Nitrogen was then bubbled through the light-yellow solution for 30 minutes, and ethyl ether (400 ml) was then added. The solution was washed with water (400 ml), saturated sodium bicarbonate (300 ml) and brine (300 ml), and was dried over anhydrous magnesium sulfate. Concentration in vacuo afforded a yellow residue, which was triturated with hexane to give, after drying over phosphorus pentoxide overnight under high vacuum, 14.72 g of 1(S)-[3-diazo-2-oxo-1-(phenylmethyl)propyl] carbamic acid, 1,1-dimethylethyl ester as a pale yellow solid. This material was used immediately in the reaction of the next step without further purification.

To a solution of the above crude diazo compound (14.72 g, 50.87 mmol) in dry ethyl ether (500 ml) cooled at 0° C. was added, dropwise, a solution of 4N hydrochloric acid in dioxane (12.72 ml, 50.87 mmol) while maintaining the temperature below 5° C. The reaction mixture was then stirred at 0° C. for one hour. Additional 4N hydrochloric acid in dioxane (636 μl 10.05 eq., 2.54 mmol) was added and the mixture was stirred at 0° C. for one additional hour. Concentration in vacuo gave a residue which was dissolved in hot ethyl ether (60 ml). Hexane (200 ml) was slowly added and the mixture was allowed to stand for 2 hours at 5° C. The solid was filtered and dried over phosphorus pentoxide under high vacuum to afford 9.58 g (first crop) of (S)-[3-chloro-2-oxo-1-(phenylmethyl)propyl]carbamic acid, 1,1-dimethylethyl ester. The filtrate was concentrated to dryness and the residue was again recrystallized from ethyl ether-hexane to give an additional 4.41 g (second crop) of (S)-[3-chloro-2-oxo-1-(phenylmethyl)propyl]carbamic acid, 1,1-dimethylethyl ester.

Sodium borohydride (1.59 g; 42 mmol) was added to a solution of (S)-[3-chloro-2-oxo-1(phenylmethyl) propyl] carbamic acid, 1,1-dimethylethyl ester (5g, 16.8 mmol) in tetrahydrofuran (84 ml) and water (9 ml) at 0° C. After stirring at 0° C. for 45 minutes the reaction mixture was concentrated to dryness. The residue was stirred at 0° C. with ethyl acetate (150 ml) and water (25 ml) while saturated potassium bisulfate solution was carefully added until the pH was about 1.5. This mixture was then diluted with ethyl acetate (350 ml) and the layers were separated. The organic layer was washed with water (100 ml) and brine (100 ml). After drying over magnesium sulfate, the organic layer was concentrated to a white solid. A portion of this solid (4.89 g) was recrystallized from hot ethyl acetate (70 ml) to afford 2.47 g of title compound as a white solid containing a small percentage of its diastereomer.

e) [S-(R*,R*)]-[2,3-Epoxy-1-(phenylmethyl) propyl]carbamic acid, 1,1-dimethylethyl ester Potassium hydroxide (0.71M) in ethanol (14.7 ml, 10.4 mmol) was added to a suspension of the product from part (d) (2.6 g, 8.67 mmol) in ethanol (87 ml) at room temperature. The reaction was stirred at room temperature for 90 minutes, during which time the thick suspension became a fine powdery one. At this time, the ethanol was removed in vacuo and the residue was partitioned between ethyl acetate (200 ml) and water (200 ml). The organic layer was washed with saturated ammonium chloride solution (2× 100 ml), water (2×100 ml), and brine (100 ml). After drying over magnesium sulfate, the ethyl acetate was removed in vacuo and the solid white residue was recrystallized by dissolving in refluxing ethyl acetate (10 ml) and adding hexane (190 ml). The resulting crystalline suspension was allowed to cool to −40° C. and kept overnight. Filtration, rinsing with hexane, and drying under high vacuum for 2 hours afforded 1.92 g of title product as a colorless crystalline solid.

f) [R-(R*,S*)]-[3-Amino-2-hydroxy-1-(phenyl methyl)propyl]carbamic acid, 1,1-dimethyl ethyl ester A solution of the product from part (e) (15.0 g, 59.96 mmol) in ethanol I (350 ml) was added, with stirring, over one hour to concentrated ammonium hydroxide (350 ml) at 0° C. Ammonia gas was bubbled through the reaction mixture during the addition and for one hour afterwards. The reaction was then warmed to room temperature and stirred overnight. The resulting slurry was diluted with ethyl acetate (800 ml) and the organic layer was washed repeatedly with brine. The organic extracts were dried over magnesium sulfate and concentrated to give a white solid. Trituration with 10% isopropanol/ethyl acetate gave 4.37 g of title product. The mother liquors were evaporated and triturated again as described above to give an additional 5.73 g of title product.

g) [1S-[1R*,2S* (2S*,3R*)]]-3-[[3-[[[(1,1-Dimethylethyl)amino] carbonyl]oxy]-2-hydroxy- 4-phenylbutyl]amino]-2-hydroxy- 1-(phenylmethyl)propyl]carbamic acid, 1,1-dimethylethyl ester A mixture of the product from part (c) (100 mg, 0.265 mmol) and the product from part (f) (98 mg, 0.35 mmol) in dimethylformamide (0.25 ml) was heated to 100° C. for 3 hours. The dimethylformamide was removed in vacuo and the residue chromatographed on a 2.5×10 cm silica gel column using 1 L methylene chloride:methanol:ammonium hydroxide, 96.75:2.50:0.25 and 1 L methylene chloride:methanol:ammonium hydroxide; 90:9:1 as the mobil phase. The fractions containing the major product were concentrated to afford 113 mg of impure product. This material was rechromatographed on a 2.5×10 cm silica gel column using methylene chloride:methanol:ammonium hydroxide, 94.5:5.0:0.5 as the mobil phase. The pure fractions were concentrated and triturated with ether to afford 62 mg of title product as a colorless crystalline solid; m.p. 97°–100° C.; $[\alpha]_D = -7.3°$ (c=0.22, methanol). TLC (methylene chloride:methanol: ammonium hydroxide, 90:9:1) $R_f = 0.24$.

Anal. calc'd for $C_{30}H_{44}N_3O_6$: C, 66.40; H, 8.17; N, 7.74 Found: C, 66.00; H, 8.33; N, 7.72.

EXAMPLE 2

[1S-[1R*,2S* (2S*,3R*)]]-[3-[[[(1,1-Dimethylethyl)amino] carbonyl]oxy]-2-hydroxy-4-phenylbutyl] amino]-2-hydroxy-1-[[4-[2-(morpholinyl)- 2-oxoethoxy]phenyl]methyl]propyl]carbamic acid, 1,1-dimethylethyl ester a) (S)-[3-Bromo-2-oxo-1-[[4-(phenylmethoxy) phenyl]methyl]propyl]carbamic acid, 1,1-dimethylethyl ester To a solution of N-[(1,1-dimethylethoxy)carbonyl]—O-benzyl-L-tyrosine in dry tetrahydrofuran (90 ml) cooled at −20° C. to −25° C. was added isobutyl chloroformate (8.7 ml, 67.3 mmol) followed by 4-methylmorpholine (6.8 ml, 67.3 mmol) and the mixture was stirred for 20 minutes. The precipitate was filtered and washed with dry tetrahydrofuran. The filtrate was cooled to −5° C. and poured into a diazomethane in ether solution (prepared from 1-methyl-3-nitro-1-nitrosoguanidine (29.7 g, 202 mmol) as described in Example 1 (d) at 0° C. The resulting yellow solution was kept at 0° C. for 2.0 hours, then at room temperature overnight. Nitrogen was then bubbled through the solution for 30 minutes, the solution diluted with ethyl ether (500 ml) and then washed with water, saturated sodium bicarbonate, and brine, and dried over magnesium sulfate. Concentration in vacuo afforded a yellow residue which was triturated with hexane (500 ml) to give 24.5 g of (S)-[3-diazo-2-oxo-1-[ [4-(phenylmethoxy)phenyl]methyl]propyl]carbamic acid, 1,1-dimethylethyl ester.

A solution of 48% aqueous hydrogen bromide (5.8 ml, 51.4 mmol) was added dropwise to the above diazo compound (20.3 g, 51.4 mmol) in 500 ml of 1,4-dioxane-1,2-dimethoxyethane (2:1) cooled to −5° C. After 30 minutes, saturated sodium bicarbonate was added until the pH was 7.0 and the solvent was removed under reduced pressure. The mixture was diluted with water and extracted with ethyl acetate. The combined organic extracts were washed with water and brine and dried over sodium sulfate. Concentration in vacuo followed by recrystallization from ethyl acetate-hexane gave 20.9 g of title product as an off-white solid.

b) [S-(R*, R*)]-[2,3-Epoxy-1-[[4-(phenylmethoxy)phenyl] methyl]propyl]carbamic acid, 1,1-dimethylethyl ester To a solution of the product from part (a) (23.3 g, 50.0 mmol) in 250 ml of methanol-tetrahydrofuran (1:1) cooled at −5° C. was added, portionwise, sodium borohydride (2.0 g, 50.0 mmol). After 1 hour, 10% potassium bisulfate (75 ml) was added at 0° C. and the mixture was allowed to warm to room temperature. The mixture was extracted with hot ethyl acetate and the combined organic extracts were washed with water and brine, and dried (sodium sulfate). Concentration in vacuo followed by recrystallization from ethyl acetate (350 ml) afforded 14.5 g (62%) of the syn bromohydrin as a white solid. HPLC analysis showed the diastereomeric ratio as 95:5. To a solution of the syn bromohydrin, prepared as above (115.2 g, 0.256 mole), in 1.5 L of tetrahydrofuran and 1.5 L of 100% ethanol was added a solution of potassium hydroxide (17.2 g of 87.6% pellets, 0.269 mole) in 300 ml of 100% ethanol at room temperature. After 15 minutes, 1 L of saturated aqueous ammonium chloride was added and the mixture then diluted with 6 L of water to give a precipitate. The solid was filtered, washed with water, and extracted into 1 L of ethyl acetate. The organic phase was dried (sodium sulfate) and concentrated in vacuo to give a solid which was triturated with 1 L of hexane to afford 79.3 g of title product as a white solid.

c) [S-(R*,R*)]-[2,3-Epoxy-1-[(4-hydroxyphenyl)methyl] propyl]carbamic acid, 1,1-dimethylethyl ester A mixture of the product from part (b) (5.0 g, 13.5 mmol) and palladium hydroxide on carbon catalyst (500 mg) in ethanol (100 ml) and ethyl acetate (25 ml) was stirred under a hydrogen atmosphere for 4.5 hours. The catalyst was removed by filtration and the filter cake was washed with ethanol, methanol and ethyl acetate. The combined washes were concentrated in vacuo to give 3.8 g of title product as a white solid.

d) [S-(R*,R*)]-[1-[[4-[2-(4-Morpholinyl)-2-oxoethoxy] phenyl]methyl]-2,3,epoxypropyl] carbamic acid, 1,1-dimethylethyl ester Sodium hydride (48 mg, 60% dispersion in mineral oil, 1.2 mmol) was washed twice with hexane and suspended in dry dimethylformamide (1 ml). The suspension was cooled to 0° C. and a solution of the product from part (c) (280 mg, 1.0 mmol) in dry dimethylformamide (1.5 ml) was added. The mixture was stirred at 0° C. for 30 minutes and then 4-(2-bromoacetyl)morpholine [J. Med. Chem., 35, 1685 (1992); 270 mg, 1.3 mmol] was added in one portion, followed by tetrabutylammonium iodide (185 mg, 0.5 mmol). The resulting mixture was stirred at room temperature overnight. After cooling to 10° C., water was added and the mixture was extracted with ethyl acetate. The combined extracts were washed with water and brine, dried over sodium bicarbonate and concentrated in vacuo to give crude product. Purification by flash chromatography (hexane-ethyl acetate, 1:1 to 1:4) on silica gel affords 392 mg of title product as a white solid.

e) [R-(R*,S*)]-[1-[[4-[2-(4-Morpholinyl)-2-oxoethoxy] phenyl]methyl]-3-amino-2-hydroxy propyl]carbamic acid, 1,1-dimethylethyl ester A solution of the product from part (d) (68 mg, 0.17 mmol) in ammonia saturated methanol (5 ml) was heated to 50° C. for 6 hours. After cooling to room temperature, the volatiles were removed in vacuo to afford 72 mg of title product as a colorless oil.

f) [1S-[1R*,2S* (2S*,3R*)]]-[3-[[3-[[[(1,1-Dimethylethyl)amino] carbonyl]oxy]-2-hydroxy- 4-phenylbutyl] amino]-2-hydroxy-1-[[4-[2-(morpholinyl)- 2-oxoethyoxy] phenylmethyl] propyl]carbamic acid, 1,1-dimethylethyl ester A mixture of the product from part (e) (65 mg, 0.15 mmol) and (1,1-dimethylethyl) carbamic acid, [S-(R*,S*)]-1-oxiranyl-2-phenylethyl ester [prepared as set forth in Example 1(c); 43 mg, 0.16 mmol] in dimethylformamide (0.2 ml) was heated at 100° C. for 5 hours. The solvent was removed in vacuo and the residue was chromatographed on a 2.5×15 cm silica gel column as follows: 200 ml of 2% methanol/ methylene chloride; 200 ml of from about 3–8% methanol/ methylene chloride +0.3–0.8% ammonium hydroxide in 1% and 0.1% increments respectively. The purest fractions were concentrated to afford 52 mg of a colorless foam. This material was further purified by preparative HPLC as follows: UV 220; YMC S-10 ODS (c-18) 30×50 mm column; stepwise gradient from 56–72% methanol/water +0.1% trifluoroacetic acid in 2% steps at 5 minute intervals; flow rate equals 35 ml/min. The fractions were eluted into test tubes containing solid sodium bicarbonate. The fractions were filtered and concentrated to a residue which was chromatographed on a 2.5×10 cm silica gel column using 5% methanol/methylene chloride + 0.5% ammonium hydroxide as the mobile phase. Concentration of product containing fractions afforded 40 mg of title product as a white solid; m.p. 72°–75° C.; $[\alpha]_D$=–5.5° (c=0.77, methanol). TLC (methylene chloride: methanol:ammmoniumhydroxide; 90:9:1) $R_f$= 0.38. Anal. calc'd for $C_{36}H_{54}N_4O_9 \cdot 0.06 H_2O$: C, 61.91; H, 7.98; N, 8.02

Found: C, 62.04; H, 8.00; N, 7.89.

EXAMPLE 3

[1S-[1R*, 2S*[2S*, 3R* (S*)]]]-(1,1-Dimethylethyl)carbamic acid, 3-[[3-[(2-hydroxy-2,3,3-trimethyl-1-oxobutyl)amino]-2-hydroxy-4-phenylbutyl]amino]-2-hydroxy-1-(phenylmethyl)propyl ester a) [R-(R*,S*)]-[3-Azido-2-hydroxy-1-(phenylmethyl) propyl]carbamic acid, 1,1-dimethylethyl ester A mixture of [S-(R*,R*)]-[2,3-epoxy-1-(phenylmethyl)propyl] carbamic acid, 1,1-dimethylethyl ester [prepared as described in Example 1 (e); 4 g, 15.2 mmol), sodium azide (2.96 g, 45.6 mmol) and ammonium chloride (1.47 g, 27.4 mmol) was refluxed in 75 ml of methanol for 5 hours. After cooling, the methanol was removed in vacuo and the residue was partitioned between ethyl acetate (200 ml) and water (100 ml). The organic layer was washed with saturated sodium bicarbonate solution (100 ml), water (100 ml) and brine (100 ml). After drying (magnesium sulfate), the organic layer was concentrated to afford 4.20 g of title product as a white solid.

b) [R-(R*, S*)]-3-Azido-2-hydroxy-1-propanamide, hydrochloride

A solution of the product from part (a) (4.1 g, 13.4 mmol) in 130 ml of saturated anhydrous hydrochloric acid in ethyl acetate was stirred for 4.5 hours at 0° C. After vigorously bubbling nitrogen through the reaction mixture, the volatiles were removed in vacuo to afford 2.87 g of title product as an off-white amorphous solid.

c) (R)-2,3,3-Trimethyl-2-hydroxybutanoic acid

A 70% solution of t-butyl hydroperoxide in water (340.5 ml, 2.38 mol) was extracted with methylene chloride (300 ml). The organic layer was added to a stirred mixture of selenium oxide (3.67 g, 33.1 mmol) and benzoic acid (8.1 g, 66.2 mmol) in methylene chloride (50 ml). The mixture was cooled to 0° C. and 2,3,3-trimethylbutene (65 g, 662 mmol) was added and the mixture was stirred at room temperature for 14 hours. The mixture was washed with 5% aqueous potassium hydroxide, brine, and dried (magnesium sulfate). The volatiles were removed by distillation and the residue was cooled to about 0° C. Acetic acid (100 ml) was added followed by the dropwise addition of methyl sulfide (100 ml) over 15 minutes. The reaction was stirred at room temperature for 3 hours, cooled to 0° C. and made basic with 20% aqueous potassium carbonate. The mixture was extracted with saturated sodium bicarbonate, dried (magnesium sulfate), and the solvent was removed by distillation at atmospheric pressure followed by distillation of the product (90°–100° C., 25 mm) to afford 20 g of 3,3-dimethyl-2-methylene-1-butanol.

Diethyl D-tartrate (618 mg, 3 mmol) and titanium isopropylate (0.744 ml, 2.5 mmol) were added to a stirred suspension of 4 Å activated powdered molecular sieves in dry methylene chloride (175 ml) at 0° C. The mixture was cooled to –20° C. and a 5.5M solution of t-butyl hydroperoxide in 2,2,4-trimethylpentane (18.2 ml, 100 mmol) was added. After 20 minutes, a solution of 3,3-dimethyl-2-methylene-1-butanol (5.7 g, 50 mmol) in methylene chloride (25 ml) was added and the mixture was stirred at –20° C. for 14 hours. After warming to 0° C., water (15 ml) was added, the mixture was stirred at room temperature for 30 minutes, 30% aqueous sodium hydroxide saturated with sodium chloride (3 ml) was added, and the reaction was stirred at room temperature for 25 minutes. The aqueous layer was extracted with methylene chloride, the combined extracts were dried (magnesium sulfate) and concentrated by distillation at atmospheric pressure by distillation at atmospheric pressure followed by distillation of 2-(1,1-dimethylethyl)-2-oxiranemethanol (105°–107° C., 25 mm; 4.75 g).

A solution of 2-(1,1-dimethylethyl)-2-oxiranemethanol (2.3 g, 17.7 mmol) in ethyl ether (10 ml) was added to a suspension of lithium aluminum hydride (1.477 g, 38.9 mmol) in ethyl ether (100 ml) at –5° C. and stirred at room temperature for 30 minutes. The mixture was cooled to 0° C., quenched with 10% aqueous sulfuric acid saturated with sodium sulfate. The aqueous layer was extracted with ethyl acetate and the combined extracts were washed with saturated sodium bicarbonate and brine and dried (magnesium sulfate). Concentration in vacuo followed by recrystallization from hexane gave 1.5 g of (R)-2,3,3-trimethyl-1,2-butanediol as a white solid.

A solution of dimethylsulfoxide (2,578 ml. 36.3 mmol) in methylene chloride (3 ml) was added dropwise at –78° C. to a stirred solution of oxalyl chloride (1.585 ml, 18.2 mmol) over 5 minutes and stirred at –78° C. for 10 minutes. A solution of (R)-2,3,3-trimethyl- 1,2-butanediol in methylene chloride (25 ml) was added dropwise and stirred for 15 minutes at –78° C. Triethylamine (11.51 ml, 82.6 mmol) was added and the reaction was allowed to come to room temperature. The mixture was diluted with additional methylene chloride, washed with 10% sulfuric acid, the combined aqueous phase was extracted with methylene chloride, and the combined organic layer was washed with saturated sodium bicarbonate, dried (magnesium sulfate), and concentrated by distillation at atmospheric pressure to afford 2.15 g of (R)-2,3,3-trimethyl-2-hydroxybutanal as a pale gummy solid.

Sodium chlorite (1.81 g, 20 mmol) and sulfamic acid (1.94 g, 20 mmol) were added in succession to a stirred solution of (R)-2,3,3-trimethyl-2-hydroxybutanal (2.0 g, 15.4 mmol) in 30 ml of tetrahydrofuran-water (1:1) at 0° C. The mixture was allowed to warm to room temperature, stirred for 30 minutes, diluted with methylene chloride and about 1 ml of methyl sulfide was added followed by a small quantity of water. The organic layer was separated, the aqueous layer was extracted with methylene chloride, and the combined organic layer was dried (magnesium sulfate) and concentrated to afford a yellow gummy solid. Recrystallization from hexanes afford 1.45 g of (R) -2,3,3-trimethyl-2-hydroxybutanoic acid as a pale solid.

d) (R)-N-[(1S, 2R) -3-Azido-2-hydroxy-1-(phenylmethyl)propyl]- 2-hydroxy-2,3,3-trimethylbutanamide Benzotriazol-1-yloxytris (dimethylamino) phosphonium hexafluorophosphate (604 mg, 1.36 mmol) was added to a solution of the product from part (b) (300 mg, 1.23 mmol), the product from part (c) (199 mg, 1.36 mmol) and 4-methylmorpholine (0.30 ml, 2.8 mmol) in dimethyl formamide (3 ml) at 0° C. After warming to room temperature and stirring for 18 hours, the reaction mixture was partitioned between ethyl acetate (50 ml) and water (50 ml). The organic layer was washed with saturated potassium bisulfate solution (2×50 ml), 1N sodium hydroxide (2×50 ml) and brine (50 ml). Drying (magnesium sulfate) and concentration afforded an oil which solidified on standing and was recrystallized from ethyl acetate/hexane to afford 186 mg of title product as a white solid.

e) (R)-N-[(1S,2R)-3-Amino-2-hydroxy-1-(phenylmethyl)propyl]- 2-hydroxy-2,3,3-trimethylbutanamide A solution of the product from part (d) (170 mg, 0.51 mmol), triphenylphosphine (150 mg, 0.56 mmol) and water (14 µl, 0.78 mmol) in tetrahydrofuran was stirred for 40 hours at room temperature. After concentration, the residue was chromatographed on a 2.5×15 cm silica gel column using 7.5% methanol/methylene chloride +0.75% ammonium hydroxide as the mobile phase. Pure fractions were concentrated to afford 142 mg of title product as an oil.

f) [1S-[1R*,2S*[2S*,3R*(S*)]]]-(1,1-Dimethylethyl)carbamic acid, 3-[[3-[(2-hydroxy-2,3,3-trimethyl- 1-oxobutyl)amino]-2-hydroxy-4-phenylbutyl] amino]-2-hydroxy-1-(phenylmethyl)propyl ester A mixture of the product from part (e) (130 mg, 0.42 mmol) and (1,1-dimethylethyl) carbamic acid, S-(R*,S*)]-1-oxiranyl-2-phenylethyl ester [prepared as described in Example 1(c); 124 mg, 0.47 mmol) in dimethylformamide (0.5 ml) was heated to 100° C. for 4 hours. The solvent was removed in vacuo and the residue was chromatographed on a 2.5×15 cm. silica gel column as follows: 200 ml 2% methanol/methylene chloride; 200 ml from about 3–6% methanol/methylene chloride +0.3–0.6 % ammonium hydroxide in 1% and 0.1% increments respectively. The pure fractions were concentrated to afford 134 mg of white solid which was triturated with ethyl acetate. Filtration and washing with hexane afforded 69 mg of title product as a white solid; m.p. 174°–178° C.; $[\alpha]_D$=23.3° (c=0.39, methanol); $[\alpha]_{365}$= 74.6° (c=0.39, methanol). TLC (methylene chloride:methanol: ammonium hydroxide; 90:9:1) $R_f$=0.36.

Anal. calc'd for $C_{32}H_{49}N_3O_6 \cdot 1.00$ $H_2O$: C, 65.16; H, 8.72; N, 7.12

Found: C, 65.21; H, 8.54; N, 7.16.

HIV Protease Assay

An HIV protease standard assay was performed in a 60 µl reaction medium containing 50 mM sodium acetate, pH 5.5, 100 µg/ml bovine serum, 450 µM substrate ($H_2N$-Val-Ser-Gin-Asn-( β-naphthyl-alanine)-Pro-Val-Ile-OH), and purified protease. The reaction medium was incubated for 30 minutes at 37° C., quenched by the addition of 140 µl 5% $H_3PO_4$, then analyzed by reverse phase HPLC using $UV_{220}$ detection. In a typical control assay, 7% of the substrate was hydrolyzed. The retrocarbamate protease inhibitors of the present invention, listed in the following Table 1, were then employed in the assay, for which purpose they were prepared as a 0.5 mM solution in DMSO then diluted to 30 µM with 50 mM sodium acetate/bovine serum albumen. This working stock was then diluted three-fold into the protease reaction medium, for a final concentration of 10 µM inhibitor and 4% DMSO. The results obtained from the assay are shown in the following Table 1.

Cell Culture Anti-HIV Activity

The antiviral activity of the retrocarbamate protease inhibitors of the present invention was evaluated by a microculture method which determines the increase in cell viability of an infected culture when a drug is added. The assay depends on the metabolic reduction of tetrazolium reagent by viable cells to yield a soluble colored formazan product.

The assay was performed as follows: suspensions of CEM—SS cells (5000/well) were infected with the RF strain of HIV at a multiplicity of infection at 0.04 in a 96-well plate. The compounds of the present invention listed in the following Table 1, serially diluted in half-log fashion, were added to the infected and uninfected control cells. Untreated (infected and uninfected) cells were included as controls. Following incubation for 6 days at 37° C., viable cells in each well were quantitated by the visible light absorbance at 450 nm.

The $IC_{50}$ was calculated as the concentration of drug that increased the formazan production in virally infected cells to 50% of that produced by uninfected cells in the absence of drug. The results obtained in the assay are shown in the following Table 1.

TABLE 1

| Compound | HIV Protease % Inhibition at 10 μM | HIV (CEM Cells) $IC_{50}$ (μM) |
| --- | --- | --- |
| Example 1 | 98 | 0.46 |
| Example 2 | 90 | 0.2 |
| Example 3 | 98 | 0.1 |

What is claimed is:

1. A compound of the formula

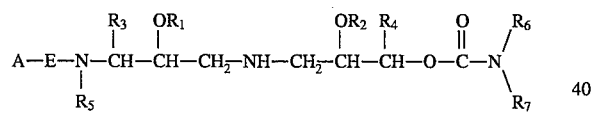

including a pharmaceutically acceptable salt thereof wherein:

$R_1$ and $R_2$ are independently selected from the group consisting of hydrogen, alkyl, substituted alkyl, alkylene-aryl, and alkylene-substituted aryl;

$R_3$ and $R_4$ are independently selected from the group consisting of hydrogen, alkyl, substituted alkyl, cycloalkyl, aryl, substituted aryl, alkylene-aryl, alkylene-substituted aryl, alkylene-cycloalkyl, and alkylene-heterocyclo;

$R_5$ is hydrogen, alkyl, substituted alkyl, alkylene-aryl, or alkylene-substituted aryl;

$R_6$ and $R_7$ are independently selected from the group consisting of hydrogen, alkyl, substituted alkyl, alkylene-aryl, and alkylene-substituted aryl and $R_6$ and $R_7$ taken together with the N-atom to which they are attached complete a heterocyclic ring of 5 to 7 atoms;

A is hydrogen, alkyl,

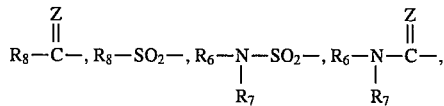

-continued

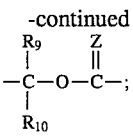

$R_8$, $R_9$ and $R_{10}$ are independently selected from the group consisting of hydrogen, alkyl, substituted alkyl, cycloalkyl, aryl, substituted aryl, alkylene-cycloalkyl, alkylene-aryl, and alkylene-substituted aryl or $R_8$ and $R_9$ join together to complete a carbocyclic ring of 3 to 7 carbon atoms;

Z is oxygen or sulfur;

E is a single bond or A—E represents the peptidyl chain

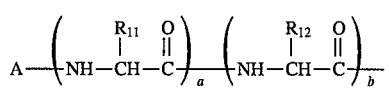

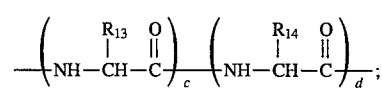

a, b, c, and d are each zero or one; and $R_{11}$, $R_{12}$, $R_{13}$ and $R_{14}$ are independently selected from the group consisting of hydrogen, alkyl, substituted alkyl, alkylene-aryl, alkylene-substituted aryl, and alkylene-heterocyclo.

2. A compound of claim 1 wherein:

E is a single bond;

$R_1$ and $R_2$ are both hydrogen;

A is

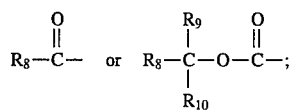

$R_3$ and $R_4$ are independently selected from the group consisting of alkylene-aryl and alkylene-substituted aryl;

$R_5$ is hydrogen;

$R_6$ is alkyl or substituted alkyl;

$R_7$ is hydrogen; and $R_8$, $R_9$, and $R_{10}$ are independently selected from the group consisting of alkyl and substituted alkyl.

3. A compound of claim 2 wherein:

A is

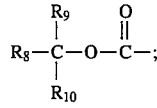

$R_3$ and $R_4$ are each benzyl;

$R_6$ is t-butyl; and $R_8$, $R_9$, and $R_{10}$ are each methyl.

4. The compound of claim 3, [1S-[ 1R*,2S*(2S*,3R*)]]-[3-[[3-[[[(1,1-dimethylethyl) amino]carbonyl]oxy]-2-hydroxy-4-phenylbutyl] amino]-2-hydroxy-1-(phenylmethyl)propyl]carbamic acid, 1,1-dimethylethyl ester.

5. A compound of claim 2 wherein:

A is

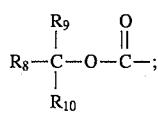

$R_3$ is

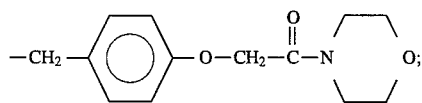

$R_4$ is benzyl;

$R_6$ is t-butyl; and $R_8$, $R_9$, and $R_{10}$ are each methyl.

6. The compound of claim 5, [1S-[1R*, 2S*(2S*,3R*)]]-[3-[[[(1,1-dimethylethyl)amino]carbonyl] oxy]-2-hydroxy-4-phenylbutyl]amino]-2-hydroxy-1-[[4-[2-(morpholinyl)-2-oxoethoxy] phenyl]methyl]propyl]carbamic acid, 1,1-dimethylethyl ester.

7. A compound of claim 2 wherein:

A is

$R_3$ and $R_4$ are both benzyl;

$R_5$ is hydrogen;

$R_6$ is t-butyl; and $R_8$ is

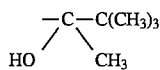

8. The compound of claim 7, [1S-[1R*, 2S* [2S*, 3R* (S*)]]]-(1,1-dimethylethyl)carbamic acid, 3-[[3-[ (2-hydroxy-2,3,3-trimethyl-1-oxobutyl)amino]-2-hydroxy-4-phenylbutyl]amino]-2-hydroxy-1-(phenylmethyl) propyl ester.

9. A pharmaceutical composition useful for the inhibition of HIV protease comprising a compound of claim 1 and a pharmaceutically acceptable carrier.

10. A method of inhibiting HIV protease comprising administering an effective amount of the composition of claim 9.

* * * * *